United States Patent [19]

Keys

[11] Patent Number: 5,674,832
[45] Date of Patent: Oct. 7, 1997

[54] CATIONIC COMPOSITIONS CONTAINING DIOL AND/OR DIOL ALKOXYLATE

[75] Inventor: Robert O. Keys, Columbus, Ohio

[73] Assignee: Witco Corporation, Greenwich, Conn.

[21] Appl. No.: 430,528

[22] Filed: Apr. 27, 1995

[51] Int. Cl.$^6$ ............................................... C11D 1/62
[52] U.S. Cl. ............................................. 510/504; 510/506
[58] Field of Search .................... 252/8.8, 8.9, 8.6, 252/547, 542, DIG. 6, DIG. 13; 510/525, 524, 522, 521, 504, 506

[56] References Cited

U.S. PATENT DOCUMENTS

| | | | |
|---|---|---|---|
| 3,915,867 | 10/1975 | Kang et al. | 252/8.8 |
| 4,140,641 | 2/1979 | Ramachandran | 252/8.75 |
| 4,184,970 | 1/1980 | Draper, Jr. | 252/8.8 |
| 4,454,049 | 6/1984 | MacGilp et al. | 252/8.8 |
| 4,769,159 | 9/1988 | Copeland | 252/8.8 |
| 4,851,141 | 7/1989 | Demangeon et al. | 252/8.75 |
| 5,284,650 | 2/1994 | Whittlinger | 424/70 |
| 5,399,272 | 3/1995 | Swartley et al. | 252/8.8 |
| 5,403,500 | 4/1995 | Turner | 252/8.8 |
| 5,427,697 | 6/1995 | Swartley | 252/8.8 |
| 5,460,736 | 10/1995 | Trinh et al. | 252/8.8 |
| 5,490,944 | 2/1996 | Suazon | 252/8.8 |
| 5,492,636 | 2/1996 | Ansari et al. | 252/8.6 |
| 5,525,245 | 6/1996 | Grandmaire et al. | 252/8.8 |

FOREIGN PATENT DOCUMENTS

| | | |
|---|---|---|
| 240727 A2 | 3/1987 | European Pat. Off. . |
| 317542 | 5/1989 | European Pat. Off. . |
| 619363 | 10/1994 | European Pat. Off. . |

OTHER PUBLICATIONS

Egan "Cationic Surface Active Agents as Fabric Softners," *J. Am. Oil. Chemists' Soc.*, 55: pp. 118–121 (Jan. 1978).
Whalley, "Fabric Conditioning Agents," *Happi*, pp. 55–58 (Feb. 1995).

*Primary Examiner*—Paul Lieberman
*Assistant Examiner*—John R. Hardee
*Attorney, Agent, or Firm*—Scully, Scott, Murphy & Presser

[57] ABSTRACT

Homogeneous liquid cationic compositions are produced by combining one or more cationic agents with one or more compounds of the formula $HO(X-O)_x-R-(O-Y)_y-OH$ wherein each X is ethylene, straight or branched propylene, or straight or branched butylene; x is 0 to 40; each Y is ethylene, straight or branched propylene, or straight or branched butylene; y is 0 to 40; the sum of (x+y) is 0 to 40; and R is saturated straight, branched or cyclic alkylene containing 4 to 12 carbon atoms or, if (x=y=0), R contains 7 to 12 carbon atoms. Compositions are easily dispersed in water, even at room temperature, at any concentration and can be made to form clear or translucent products having a desirable uniform appearance, by appropriate selection of components and their amounts.

12 Claims, No Drawings

CATIONIC COMPOSITIONS CONTAINING DIOL AND/OR DIOL ALKOXYLATE

BACKGROUND OF THE INVENTION

The present invention relates to liquid formulations containing one or more cationic compounds, such as: liquid fabric softeners of the type conventionally employed in the rinse cycle of automatic clothes washing machines; liquid textile softeners used for fabric finishing; compositions used in the paper industry for debonding and softening of paper fibers; hair and skin conditioners; compositions applied to clay-based products such as drilling muds to make them hydrophobic; and many other uses.

The present invention relates more particularly to novel compositions for liquid cationic formulations, wherein the ingredients of the composition contribute significantly to the ease of formulation, stability, dispersibility, fluidity and the performance properties of the compositions.

Cationics have achieved widespread usage because of their ability to impart to fabric, (i.e. articles of clothing, textiles, and so forth), paper, hair, and many other substrates, properties including softness to the touch, ease of handling, increased lubricity, and a reduced tendency to carry or pick up static electricity. One form in which cationics are provided is as a liquid, for instance as an emulsion or as a solution/suspension of the desired components. An appropriate controlled amount of the liquid cationic formulation is employed (poured into the washing machine or textile bath in which the fabric is being washed or rinsed; or applied to the hair; or added to the head tank of the paper making machine, or otherwise depending on the application).

Typically, in the case of liquid fabric softeners it is provided during the rinse cycle of the washing machine, either poured in by hand or metered in by an appropriate automatic metering device with which the washing machine is equipped. In the same vein, cationics (typically dialkyl quaternaries) are used in textile mills to add lubricity and finishing to the fabric prior to shipping the textile to market. The mill applies the cationic formulation in dilute emulsions and rapidly dries the excess water from the fabric. The fibers are thus lubricated and given a surface finish. Hair conditioners are applied as dilute cationic emulsions to the hair following its wash. Adding these conditioners (typically dialkyl quaternaries) reduces the tendency for tangling, improves the manageability, and imparts a soft feel to the hair strands. In the papermaking process, cationics called debonders are generally quaternary salt emulsions in water. These are added to the head tank wherein the dilute fibers are conditioned with the debonders just prior to being fed onto the papermaking screen. These debonders give improved softness feeling to the paper fibers. In all cases the cationics are added to hot water to make an emulsion, and then added to the substrate in water or added to the substrate in water or added as a high solids concentrate to the substrate, to impart softness, lubricity, antistatic properties, ease of handling of the substrate and to improve surface appearance.

It is believed that the user finds it to be desirable that the liquid cationic formulation is in the form of a moderately viscous fluid, rather more viscous than water yet still capable of flowing under its own weight. Thus, for instance, having a formulation that at solids concentrations of less than 5% exhibit viscosities greater than 100 cps which would be effective in softening and disperse readily in cold water, such as the present invention, would be desirable in the marketplace. In other cases, the industrial user may want less viscous, fluid emulsions or concentrates that disperse easily, with fine particle sizes.

In the case of fabric softeners, formulations which would be low melting (compared to many softener raw materials which must be heated to 90°–120° F.) and are easily dispersed in room temperature water would save time and money in both equipment and production costs.

High solids formulations (or "ultras") which have solids contents greater than 20% have seen large commercial success over the last five years. The drive to increase solids contents, and to reduce handling and transportation costs is becoming ever more important. The desire ultimately to form a clear, highly active, high performance product when the product is dispersed in water is becoming an important objective. The standard emulsion type fabric softener ultras in the market suffer from thickening problems following production, causing reduced dispersibility in the rinse cycle.

There is a need for cationic formulations, including fabric softeners, which are nonflammable yet easy to handle and disperse in room temperature water. Most quaternary formulations contain isopropanol or ethanol as solvents in order to aid in production and handling. However, volatile solvents such as these are becoming an important environmental issue in states including California and Florida. Thus, a different technique for achieving fluidity and good dispersiblity, while avoiding the use of volatile solvents, is needed. Also, as interest grows in dilutable concentrated product which can be diluted by the customer (e.g. by 3–10 times) to make a regular (2–10%) concentration of the product as used, the need for making such products that are easily dispersible without resort to volatile or flammable solvents is very important.

Thus, there is still a need in this field for liquid cationic formulations which can be prepared more readily without encountering difficulties such as those described above, and are more concentrated and disperse easily in cold water. There is also a need in this field for cationic formulations which can be manufactured as concentrates, wherein formulators can produce consumer and industrial products easily, quickly and effectively with minimal equipment and heating requirements. There is also a need for products (especially for use in the textile and paper areas) which are not flammable but which avoid the handling and viscosity problems posed by the conventional less flammable substitutes such as propylene glycol, diethylene glycol and the like.

The prior art concerning various cationic compositions is extensive, yet has not taught or suggested the considerable and unexpected benefits that are provided by the formulations which correspond to the present invention. For instance, U.S. Pat. No. 5,399,272 discloses a clear or translucent liquid fabric softening composition containing any of certain ester-quaternary cationic compounds. The disclosure also requires any of certain alcohols, glycols, esters or ethers as solvent.

However, the disclosure of U.S. Pat. No. 5,399,272 also requires a second quaternary compound and/or an amine oxide to serve as a dispersibility aid. The requirement for this dispersibility aid serves as a teaching that the disclosed solvent system does not adequately provide needed dispersiblity on its own, that is, in the absence of a dispersibility aid. This teaching thus serves to confirm the present state of the art, namely, that there remains a need for formulations which serve to solubilize and disperse cationic active agents without needing to resort to the addition of dispersibliity aids. After all, extra dispersibliity aids will add to the cost of materials, and having to add another cationic to the formulation could in some cases interfere with obtaining desired fluidity, maintaining a monophasic state, or obtaining the desired performance properties.

The present invention satisfies the needs identified above, and provides as well additional advantages that will become apparent in the following description.

BRIEF SUMMARY OF THE INVENTION

One aspect of the present invention comprises homogeneous aqueous liquid compositions comprising (a) one or a combination of compounds of the formula (1)

$$HO-(X-O)_x-R-(O-Y)_y-OH \qquad (1)$$

wherein each X is ethylene, straight or branched propylene or straight or branched butylene; x is 0–40; each Y is ethylene, straight or branched propylene, or straight or branched butylene; y is 0–40; the sum of (x+y) is 0–40; and R is straight, cyclic or branched alkylene containing 4–12 carbon atoms, provided that if x and y are both zero then R contains 7 to 12 carbon atoms; and (b) one or more cationic agents. In many embodiments, the component (b) comprises two or more cationic agents, i.e., quaternary ammonium compounds and/or amine salts as described herein.

Another aspect of the present invention comprises highly concentrated homogeneous compositions having the aforementioned composition, which concentrates are easily dispersible in water.

Another aspect of the present invention comprises the method of manufacturing a homogeneous liquid cationic composition, by combining one or more compounds of the aforementioned formula (1), water, and one or more cationic agents under conditions to form a homogeneous liquid product therefrom.

DETAILED DESCRIPTION OF THE INVENTION

The compounds of the aforementioned formula (1), sometimes referred to herein as diols and diol alkoxylates, contribute essentially to many of the advantageous properties of the compositions of the present invention. In formula (1), the molecule can comprise one or two terminal poly(alkoxy) chains. While, as defined above, each alkoxy unit can be ethoxy, propoxy, or butoxy, a mixture of types of alkoxy groups, or block copolymers composed of a chain of one type of repeating alkoxy unit attached to a chain of a different type of repeating alkoxy unit, are especially contemplated.

The alkylene residue R in formula (1) represents a saturated, straight-chain, branched-chain, or cyclic moiety containing 4 to 12 carbon atoms. It is preferred that R is branched; the term "branched" is intended to encompass structures having one side alkyl chain, more than one side alkyl chain, or one or more side alkyl chains one or more of which is itself branched. Branched structures include cyclic structures substituted with one or more alkyl groups which can be straight or branched. Examples of suitable R groups include —CH$_2$CH$_2$CH$_2$—, —C(CH$_3$)CH$_2$—, —CH$_2$CH(CH$_3$)CH$_2$—, —CH$_2$C(CH$_3$)$_2$CH$_2$—, —CH$_2$CH(CH$_2$CH$_2$CH$_2$CH$_3$)—, —(CH$_2$)$_6$—,

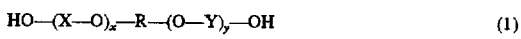

—CH$_2$C(CH$_3$)$_2$CH(CH(CH$_3$)$_2$)—, and —CH$_2$CH(CH$_2$CH$_3$)CH$_2$CH$_2$CH$_2$CH$_2$—.

In the alkoxylated diols, the number of repeating units in each poly(alkoxy) chain can be up to 40 but it is preferred that each chain contains 1 to 10 repeating alkoxy units or more preferably 1 to 5 alkoxy units. The preferred alkoxy chains are poly(ethoxy), or are composed of 1 to 2 ethoxy units capped with a chain of 1 to 5 propoxy units.

Compounds of the formula (1) defined above are in many instances commercially available. Compounds of formula (1) can be prepared in straightforward manner familiar to those of ordinary skill in this art by obtaining or preparing the corresponding precursor diol of the formula HO—R—OH, and then alkoxylating the precursor diol with a stoichiometrically appropriate number of moles of the desired corresponding alkylene oxide, such as ethylene oxide, propylene oxide, and/or butylene oxide. In those cases where it is desired to alkoxylate only one of the hydroxyl groups on the precursor diol, in some embodiments the alkoxylation will preferentially occur at only one of the hydroxyl groups, particularly where one of them is a primary hydroxyl and the other is a secondary hydroxyl. However, in those cases where both hydroxyl groups on the precursor diol might tend to alkoxylate but alkoxylation at only one of the hydroxyl groups is desired, the hydroxyl group at which alkoxylation is desired not to occur can be protected by preliminarily reacting it with a suitable protecting group such as a lower alkyl moiety or an esterifying substituent. Thereafter, following the alkoxylation, the protecting group is removed in a known manner.

Preferred examples of compounds of the foregoing formula (1) include any one, or mixtures, of 2,2,4-trimethyl-1,3-pentane diol (referred to herein as "TMPD") and/or 2-ethylhexane-1, 3-diol, and/or the reaction product of TMPD and/or 2-ethylhexane-1, 3-diol with 1 to 10 moles of ethylene oxide, and preferably with 2 to 5 moles of ethylene oxide, as well as analogs alkoxylated with other C$_3$ or C$_4$ alkyl oxides or mixtures of any of C$_2$, C$_3$ and/or C$_4$ alkyl oxides. Since the diol which is alkoxylated includes one primary hydroxyl group and one secondary hydroxyl group, the alkoxylation proceeds predominately at the primary hydroxyl group.

The cationic component of the present invention is one compound, or a combination of more than one compound, which compound or combination exhibits or imparts to the final product the properties desired for the intended use. Those properties include imparting to fabric, textiles, paper fibers, hair and other substrates a feeling of increased softness to the touch and a reduced tendency to carry or pick up static electricity.

Compounds one or more of which make up the cationic component, are typically nitrogenous compounds, e.g. secondary or tertiary amines, quaternary ammonium compounds, amine salts and diamine and triamine counterparts thereof.

As indicated, the present invention and its attendant advantages are realized with any cationic agent and particularly those which are mono- or di-(long chain alkyl) derivatives. Without intending to limit the scope of this invention, the following are provided as examples of cationic agents that can be employed in the present invention. That is, the present invention is intended to extend to compositions containing any other cationic compound that may not be mentioned herein.

Cationic agents usable in the present invention include, but are not limited to, nitrogenous compounds selected from the group consisting of quaternized or acid salt derivatives of:

(i) alkylenediamines including compounds of the formula:

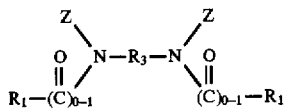

wherein each $R_1$ is an acyclic alkyl or alkylene $C_{12}$–$C_{21}$ hydrocarbon group, each Z is —$(R_2O)_{0-4}H$, or —$R_2H$, and $R_2$ and $R_3$ are divalent $C_1$–$C_6$ alkylene groups;

(ii) substituted imidazoline compounds having the formula:

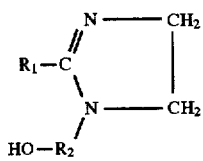

(iii) substituted imidazoline compounds having the formula:

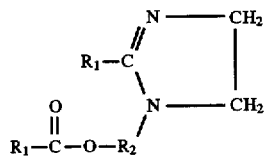

wherein $R_1$ and $R_2$ are defined as above;

(iv) reaction products of higher fatty acids with alkylenetriamines in, e.g., a molecular ratio of about 2:1, said reaction products containing compounds of the formula:

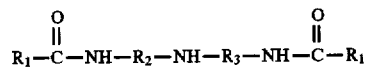

wherein $R_1$, $R_2$ and $R_3$ are defined as above;

(v) substituted imidazoline compounds having the formula:

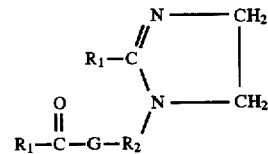

wherein G is —O— or —NH— and $R_1$ and $R_2$ are defined as above; and mixtures thereof.

Preferred examples of compounds of formula (i) are those derived from hydrogenated tallow fatty acids and the hydroxyalkylalkylenediamine N-2-hydroxyethylethylenediamine, such that $R_1$ is an aliphatic $C_{15}$–$C_{21}$ hydrocarbon group, and $R_2$ and $R_3$ are divalent ethylene groups.

A preferred example of compounds of formula (ii) is stearic hydroxyethyl imidazoline wherein $R_1$ is an aliphatic $C_{21}$ hydrocarbon group and $R_2$ is a divalent ethylene group.

A preferred example of compounds of formula (iv) is N,N"-ditallowalkanoyldiethylenetriamine where $R_1$ is an aliphatic $C_{15}$–$C_{21}$ hydrocarbon group and $R_2$ and $R_3$ are divalent ethylene groups.

A preferred example of compounds of formula (v) is 1-tallowamidoethyl-2-tallowimidazoline wherein $R_1$ is an aliphatic $C_{15}$–$C_{21}$ hydrocarbon group and $R_2$ is a divalent ethylene group.

Both N,N"-ditallowalkanoyldiethylenetriamine and 1-tallowethylamido-2-tallowimidazoline are reaction products of tallow fatty acids and diethylenetriamine, and are precursors of the cationic fabric softening agent methyl-1-tallowamidoethyl-2-tallowimidazolinium methylsulfate (see "Cationic Surface Active Agents as Fabric Softeners," R. R. Egan, Journal of the American Oil & Chemicals Society, January 1978, pages 118–121). N,N"-ditallowalkanoyldiethylenetriamine and 1-tallowamidoethyl-2-tallowimidazoline can be obtained from Witco Corporation. Methyl-1-tallowamidoethyl-2-tallowimidazoliniummethylsulfate is sold by Witco Corporation under the trade name Varisoft® 475.

Other useful softening agents include cationic nitrogenous quaternary ammonium compounds and salts. In the cationic nitrogenous salts herein, the anion A⊖ provides electrical neutrality. Most often, the anion used to provide electrical neutrality in these salts is a halide, such as chloride, bromide, or iodide. However, other anions can be used, such as methylsulfate, ethylsulfate, acetate, formate, sulfate, carbonate, and the like. Chloride and methylsulfate are preferred herein as the anion $A^-$.

One type of cationic compounds are those containing one long chain acyclic aliphatic $C_8$–$C_{22}$ hydrocarbon group, selected from the group consisting of:

(vi) acyclic quaternary ammonium salts having the formula:

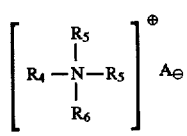

wherein $R_4$ is an acyclic aliphatic $C_8$–$C_{22}$ hydrocarbon group, alkyl, benzyl or ($C_4$–$C_{18}$ alkyl)—(OCH$_2$CH$_2$)$_{2-3}$—. $R_5$ and $R_6$ are $C_1$–$C_4$— saturated alkyl or hydroxyalkyl groups and A⊖ is an anion;

(vii) substituted imidazolinium salts having the formula:

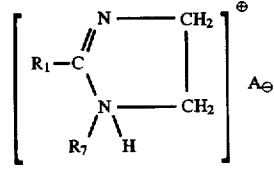

wherein $R_1$ is an acyclic alkyl or alkylene $C_{12}$–$C_{21}$ hydrocarbon group, $R_7$ is hydrogen or a $C_1$–$C_4$ saturated alkyl or hydroxyalkyl group, and Aβ is an anion;

(viii) substituted imidazolinium salts having the formula:

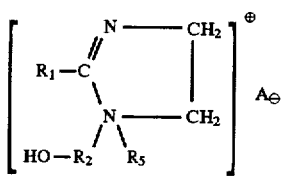

wherein $R_1$, $R_2$, $R_5$ and $A\ominus$ are as defined above;

(ix) diquaternaries of the formula

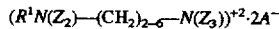

wherein $R_1$ and each Z are independently as defined above;

(x) alkylpyridinium salts having the formula:

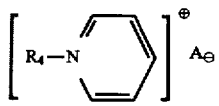

wherein $R_4$ is an acyclic aliphatic $C_8$–$C_{22}$ hydrocarbon group and $A\ominus$ is an anion; and (xi) alkanamide alkylene pyridinium salts having the formula:

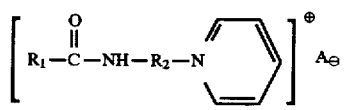

wherein $R_1$ is an acyclic aliphatic $C_{12}$–$C_{21}$ hydrocarbon group, $R_2$ is a divalent $C_1$–$C_6$ alkylene group, and $A\ominus$ is an anion; and mixtures thereof.

Examples of compound (vi) are the monoalkyltrimethylammonium salts such as monotallowtrimethylammonium chloride, mono(hydrogenated tallow)-trimethylammonium chloride, palmityltrimethylammonium chloride and soyatrimethylammonium chloride, sold by Witco Corporation under the trade names Adogen 471, Adogen 441, Adogen 444, and Adogen 415, respectively. In these compounds, $R_4$ is an acyclic aliphatic $C_{16}$–$C_{18}$ hydrocarbon group, and $R_5$ and $R_6$ are methyl groups. Mono(hydrogenated tallow) trimethylammonium chloride and monotallowtrimethylammonium chloride are preferred. Other examples of compound (vi) are behenyltrimethylammonium chloride wherein $R_4$ is a $C_{22}$ hydrocarbon group and sold under the trade name Kemamine® Q2803-C by Humko Chemical Division of Witco Corporation; soyadimethylethylammonium ethylsulfate wherein $R_4$ is a $C_{16}$–$C_{18}$ hydrocarbon group, $R_5$ is a methyl group, $R_6$ is an ethyl group, and $A^-$ is an ethylsulfate anion; and methyl bis(2-hydroxyethyl) octadecylammonium chloride wherein $R_4$ is a $C_{18}$ hydrocarbon group, $R_5$ is a 2-hydroxyethyl group and $R_6$ is a methyl group.

An example of compound (viii) is 1-ethyl-1-(2-hydroxyethyl)-2-isoheptadecylimidazolinium ethylsulfate wherein $R_1$ is a $C_{17}$ hydrocarbon group, $R_2$ is an ethylene group, $R_5$ is an ethyl group, and $A^-$ is an ethylsulfate anion.

Other fabric softening agents useful in the present invention include cationic nitrogenous salts having two or more long chain acyclic aliphatic $C_8$–$C_{22}$ hydrocarbon groups or one said group and an arylalkyl group. Examples include:

(xii) acyclic quaternary ammonium salts having the formula:

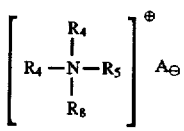

wherein each $R_4$ is an acyclic aliphatic $C_8$–$C_{22}$ hydrocarbon group, $R_5$ is a $C_1$–$C_4$ saturated alkyl or hydroxyalkyl group, $R_8$ is selected from the group consisting of $R_4$ and $R_5$ groups, and $A\ominus$ is an anion defined as above;

(xiii) diamido quaternary ammonium salts having the formula:

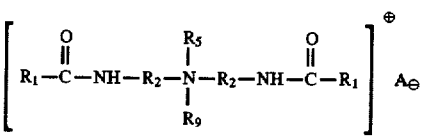

wherein each $R_1$ is an acyclic alkyl or alkylene $C_{12}$–$C_{21}$ hydrocarbon group, each $R_2$ is a divalent alkylene group having 1 to 3 carbon atoms, $R_5$ and $R_9$ are $C_1$–$C_4$ saturated alkyl or hydroxyalkyl groups, and $A\ominus$ is an anion;

(xiv) alkoxylated diamido quaternary ammonium salts having the formula:

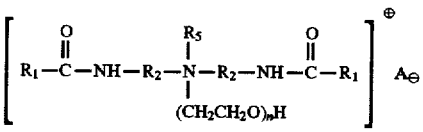

wherein n is equal to 1 to about 5, and $R_1$, $R_2$, $R_5$ and $A\ominus$ are as defined above;

(xv) quaternary ammonium compounds having the formula:

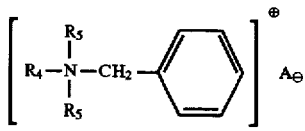

wherein each $R_4$ is an acyclic aliphatic $C_8$–$C_{22}$ hydrocarbon carbon group, each $R_5$ is a $C_1$–$C_4$ saturated alkyl or hydroxyalkyl group, and $A\ominus$ is an anion;

(xvi) amide-substituted imidazolinium salts having the formula:

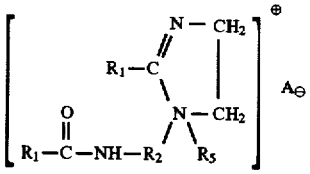

wherein each $R_1$ is an acyclic aliphatic $C_{12}$–$C_{21}$ hydrocarbon group, $R_2$ is a divalent alkylene group having 1 to 3 carbon atoms, and $R_5$ and $A\ominus$ are as defined above or $R^5$ is —H; and (xvii) ester-substituted imidazolinium salts having the formula:

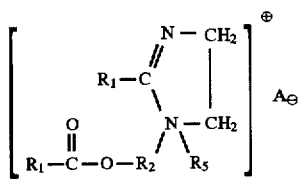

wherein $R_1$, $R_2$, $R_5$ and $A^\ominus$ are as defined above; and mixtures thereof.

Examples of compound (xii) are the well-known dialkyldimethylammonium salts such as ditallowdimethylammonium chloride, ditallowdimethylammonium methylsulfate, di(hydrogenated tallow)dimethylammonium chloride, distearyldimethylammonium chloride, dibehenyldimethylammonium chloride. Di(hydrogenated tallow) dimethylammonium chloride and ditallowdimethylammonium chloride are preferred. Examples of commercially available dialkyldimethylammonium salts usable in the present invention are di(hydrogenated tallow)dimethylammonium chloride (trade name Adogen 442), ditallowdimethylammonium chloride (trade name Adogen 470), distearyldimethylammonium chloride (trade name Arosurf TA-100), all available from Witco Corporation. Dibehenyldimethylammonium chloride wherein $R_4$ is an acyclic aliphatic $C_{22}$ hydrocarbon group is sold under the trade name Kemamine Q-2802C by Humko Chemical Division of Witco Corporation.

Examples of compound (xiii) are methylbis (tallowamidoethyl) (2-hydroxyethyl)ammonium methylsulfate and methylbis(hydrogenated tallowamidoethyl)(2-hydroxyethyl)ammoniummethylsulfate wherein $R_1$ is an acyclic aliphatic $C_{15}$–$C_{17}$ hydrocarbon group, $R_2$ is an ethylene group, $R_5$ is a methyl group, $R_0$ is a hydroxyalkyl group and $A^-$ is a methylsulfate anion; these materials are available from Witco Corporation under the trade names Varisoft 222 and Varisoft 110, respectively.

An example of compound (xv) is dimethylstearylbenzylammonium chloride wherein $R_4$ is an acyclic aliphatic $C_{18}$ hydrocarbon group, $R_5$ is a methyl group and $A^-$ is a chloride anion, which is sold under the trade name Varisoft SDC by Witco Corporation.

Examples of compound (xvi) are 1-methyl-1-tallowamidoethyl-2-tallowimidazolinium methylsulfate and 1-methyl-1-(hydrogenated tallowamidoethyl)-2-(hydrogenated tallow)imidazolinium methylsulfate wherein $R_1$ is an acyclic aliphatic $C_{15}$–$C_{17}$ hydrocarbon group, $R_2$ is an ethylene group, $R_5$ is a methyl group and $A^-$ is a chloride anion; they are sold under the trade names Varisoft 475 and Varisoft 445 respectively, by Witco.

Additional examples of fabric softening compounds useful in the present invention include (xviii) compounds characterized by the formula:

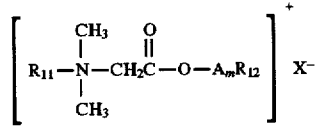

wherein $R_{11}$ is a radical selected from the group consisting of (a) straight chain aliphatic hydrocarbon radicals each of which contains from 12 through 24 carbon atoms, (b) ether radicals each of which has the structure: $R_{13}O(CH_2O)_y$—, (c) amide radicals each of which has the structure:

and (d) ester radicals each of which has the structure:

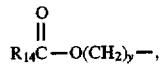

$R_{12}$ is a straight chain aliphatic hydrocarbon radical containing from 12 to 32 carbon atoms.

$R_{13}$ is a straight chain aliphatic hydrocarbon radical containing from 8 to 18 carbon atoms.

$R_{14}$ is a straight chain aliphatic hydrocarbon radical containing from 7 to 17 carbon atoms.

A is an alkoxy radical containing one oxygen atom and either two or three carbon atoms.

X is an atom selected from the group consisting of bromine and chlorine.

m is an integer of from 1 through 12, and y is an integer which is either 2 or 3.

Yet additional examples of fabric softening compounds useful in the present invention include (xix) compounds having the formula:

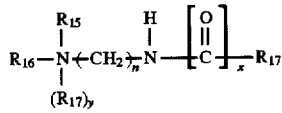

wherein each $R_{15}$ is selected from the group consisting of hydrogen and $C_1$–$C_4$ alkyl, each $R_{16}$ is selected from the group consisting of $C_1$–$C_4$ alkyl and

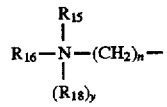

each $R_{17}$ is selected from the group consisting of $C_8$–$C_{28}$ alkyl and alkenyl groups, each $R_{18}$ is selected from the group consisting of hydrogen and $C_1$–$C_4$ alkyl, each y is 0 or 1, x is 0 or 1 and each n is from 1 to 6;

(xx) amides represented by the formula:

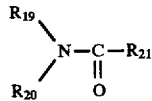

wherein $R_{19}$ and $R_{20}$ are, selected independently, $C_{1-22}$ alk(en)yl aryl, or alkyl aryl groups, $R_{21}$ is hydrogen, or a $C_{1-22}$ alk(en)yl, aryl or alkyl-aryl group, or is O—$R_4$, wherein $R_{22}$ is a $C_{1-2}$ alk(en)yl, aryl or alkyl-aryl group, and $R_{21}$ and $R_{22}$ possibly containing 1 to 10 ethylene oxide units, or functional groups selected from hydroxy, amine, amide, ester, and ether groups; the aryl groups being possibly derived from hetero-cyclic compounds; at least one of the $R_{19}$ and $R_{20}$ groups contains 10 or more carbon atoms; the sum of carbon atoms in $R_{19}+R_{20}+R_{21}$ is equal to or greater than 14. Preferably, the sum of carbon atoms in $R_{19}+R_{20}$ is equal to or greater than 16.

Such species include N,N-ditallow acetamide, N,N-dicoconut acetamide, N,N-dioctadecyl propanamide, N-dodecyl, N-octadecyl acetamide, N-hexadecyl, N-dodecyl butanamide, N,N-ditallow benzamide, N,N-dicoconut benzamide, and N,N-ditallow 2-phenyl acetamide.

Additional fabric softening compounds useful in the present invention include all ester-quaternaries, including but not limited to:

(xxi) compounds of any of the formulas $$R^{21}-C(O)-(O-(Alk^{21}))_{1-4} \diagdown \diagup Q^{21a}$$
$$N^+ \quad X^-$$
$$R^{21}-C(O)-(O-(Alk^{21}))_{1-4} \diagup \diagdown Q^{21b}$$

$$R^{21}-C(O)-O-CH-(CH_2)_{0-3}N^+-Q^{21a}X^-$$
$$| \qquad\qquad\qquad\qquad |$$
$$R^{21}-C(O)-O-(CH_2)_{1-3} \qquad Q^{21b}$$

wherein each $R^{21}$ is independently a saturated or unsaturated alkyl or alkylene radical containing 12 to 22 carbon atoms;

$Q^{21a}$ and $Q^{21b}$ are alkyl containing 1 to 4 carbon atoms or benzyl, $-CH_2CH_2OH$, or $-CH_2CH(OH)CH_3$, or $Q^{21a}$ can be $R^{21}-C(O)-(O-(Alk^{21}))_{1-4}-$;

each $Alk^{21}$ is independently $C_2H_4$, $C_3H_6$ or $C_4H_8$;

$R^2$ is alkyl containing 1 to 4 carbon atoms or benzyl, $-CH_2CH_2OH$ or $-CH_2CH(OH)CH_3$; and $X^-$ is an anion;

(xxii) compounds of the formula $$A^{22} \diagdown \diagup (CH_2)_{2-4}-X^{22}$$
$$(A^{22}-N-(CH_2)_{2-6}-N)^{+(i+j)} \cdot n(Z^{22})^{-1}$$
$$(A^{22})_i \qquad (D)_j \quad (CH_2)_{2-4}-X^{22}$$

wherein each $A^{22}$ is the same or different and each is alkyl containing up to 3 carbon atoms, benzyl, or $H-(Alk^{22}-O)_{1-3}-Alk^{22}-$ wherein each $Alk^{22}$ signifies $-CH_2CH_2-$, $-CH(CH_3)CH_2-$, or $-CH_2CH(CH_3)-$, provided further that one of the $A^{22}$ can be hydrogen;

D is methyl, ethyl, propyl, $-(CH_2)_{1-3}COO^-$, benzyl or hydrogen;

i is 0 or 1 and j is 0 or 1, provided that the sum of (i+j) is 1 or 2;

each $X^{22}$ is a straight or branched saturated or unsaturated aliphatic group containing up to 3 carbon-carbon double bonds and containing 11 to 23 carbon atoms;

n is (two minus the number of $-(CH_2)_{1-3}COO^-$ substituents present); and $Z^{22}$ is an anion;

(xxiii) compounds of the formula $$R^{23}-[C(O)O(CH_2)_{1-5}]_{0-1}-C(O)NH(CH_2)_{2-5}-N(R^{23a})(R^{23b})-$$
$$(CH_2)_{2-5}-OC(O)R^{23}X^{31}$$

wherein each $R^{23}$ is independently straight or branched alkyl or alkenyl containing 8 to 22 carbon atoms;

$R^{23a}$ is straight or branched alkyl or hydroxyalkyl containing 1 to 3 carbon atoms, benzyl, or $-C_2H_4OC(O)R_4$ wherein $R^4$ is straight or branched alkyl or alkenyl containing 8 to 22 carbon atoms;

$R^{23b}$ is H, $-CH_3$, $-C_2H_5$ or benzyl; and $X^-$ is an anion.

(In the foregoing, "Adogen", "Arosurf" and "Varisoft" are trademarks of Witco Corp.)

The cationic compositions of the present invention also contain water but are diluted into or by water in each application area.

The amounts of the cationic component, the one or more components corresponding to formula (1), and water, can vary within relatively large ranges, depending upon the degree of concentration of the components desired, and depending also on the particular characteristics of the particular components selected. The cationic component should be present in an amount at least sufficient to afford the desired effect (i.e. fabric or textile softening, paper debonding, hair conditioning, and so forth, as the case may be) and can be present in amounts substantially higher representing commercial concentrations on the order of 5–25 wt. % up to amounts on the order of 30 percent or higher, up to 60, 70, 80 or even 90 wt. % of the composition. These higher contents represent concentrates from which useful compositions can be formulated upon dilution or used as is, if desired due to their dispersibility in water.

The component of formula (1) is present in an amount sufficient to form with the cationic component a phase-stable, water-dispersible formulation. In general, satisfactory amounts of the one or more compounds of formula (1) correspond to a weight ratio with respect to the amount of cationic component present of 1:30 to 5:1 (diol or diol alkoxylates:fabric softener), and preferably 1:10 to 1:1.

The fabric softening compositions of the present invention can also contain conventional additives known to those familiar with this field, including colorants, fragrances, preservatives, and the like. In addition, if desired a small but effective amount up to about 2 wt. % of one or more inorganic salts, such as sodium chloride or calcium chloride, can be added to adjust the viscosity of the composition. Other components that can be present, and often are present, include monoalkyl nonionic materials such as fatty alcohols, fatty acid ethoxylates and propoxylates, monoalkyl esters or poly(ethylene glycol) esters of fatty acids, polysiloxanes, and amine-funcional polysiloxanes; other cationic surfactants; solvents such as short chain alcohols with up to about 6 carbon atoms (e.g. ethanol, isopropanol); lower glycols and glycol ethers, containing up to about 12 carbon atoms, such as ethylene glycol, diethylene glycol, propylene glycol, propylene glycol ether, propylene glycol butyl ether, and the like; polyethylene glycols; polypropylene glycols; fatty ethers; and hydrocarbons.

Compositions having the foregoing characteristics can readily be prepared by simply stirring together in appropriate equipment the diol and/or diol alkoxylate component, with the one or more compounds constituting the cationic component, into the water, along with any other desired additives.

The cationic compositions of the present invention afford a number of advantages not heretofore contemplated. One advantage is ease of formulation of these cationic compositions. Conventionally, emulsion-based cationic formulations can be made to a concentration of up to about 25 wt. % solids, employing high shear and requiring the addition of a salt such as calcium chloride for viscosity control. Solvent based (clear or transparent) cationic formulations can be made conventionally containing about 40 to about 60 wt. % solids, but often go through a gel-like phase which is very difficult to disperse, such that an acceptably uniform dispersion of the cationic component can be impossible to achieve. They normally require large levels (e.g. 10% or more) of flammable solvent such as isopropanol or ethanol, and/or hexylene glycol or propylene glycol, to formulate.

On the other hand, compositions prepared in accordance with the present invention exhibit a noticeable ease of dispersibility in water at any concentration level and can be thinned by adding $CaCl_2$ to form clear, fluid formulations. This is quite unique compared to those compositions outside the scope of the present invention requiring additions of e.g. isopropanol and/or ethanol and/or hexylene glycol, which revert back to the emulsion when salts are added. Much higher levels of alcohol and short-chained glycols are needed to maintain fluidity in such compositions. As much as 2 to 5 times more of such conventional solvents or coupling agents are needed for acceptable fluidity than is the case using the $C_7$–$C_{12}$ diols and diol alkoxylates in accordance with the present invention. In addition, the compositions of the present invention do not readily gel when added to water for purposes of dilution. Thus, products of a concentration useful in the home can be prepared from concentrates very easily by simply dispersing an appropriate amount of the concentrate into room temperature water.

Another advantage is the appearance of the product. An opaque fabric softener or other cationic product is less desirable both because the appearance is considered to be unattractive to the consumer and also because it indicates that the distribution of the fabric softening components in the composition is not homogeneous. In the case of fabric softeners, this possibly results in uneven deposition of the fabric softener component on the clothing and possibly even results in staining of the fabric by the fabric softener component. On the other hand, fabric softener and other cationic compositions in accordance with the present invention can be made to appear clear or translucent, and upon addition of high amounts of water quickly form a correspondingly milky or clear, uniform product appearance. The iodine value (I.V.) of the cationic quaternaries to obtain clear formulations must be at least about 50 and is more preferably 60–90. Quaternaries derived from oleyl or soft tallow fatty acids especially can be made to give clear formulations.

The ease of formulation and dispersibility has other beneficial effects, including reduction in heating costs for formulators (who conventionally must heat the blend of components to help achieve the desired uniformity of distribution), and reduction in the amount of energy expended in mixing and transport. These features make it feasible to sell highly concentrated cationic formulations directly to the user, who prepares products having the concentrations conventionally employed from the concentrate by diluting an appropriate small quantity of concentrate with tap water or by adding it directly (for instance, by adding a small amount of a fabric softener concentrate) into the automatic dispenser on the machine where it is diluted and added to the rinse cycle.

Thus, both the emulsion type, clear and even clear gels can be made using the techniques disclosed herein. The diol of formula (1) allows the cationic agent to be dispersed into water or to be diluted with water to any of a wide variety of concentrations and physical states (e.g. gels, clear products, and emulsions).

The following examples, which are intended for purposes of illustration and not intended to limit the scope of the protection sought for the invention described herein:

EXAMPLE 1

Preparation of Diol Alkoxylate

To a 2-liter Parr reactor was charged 438 grams (3.0 moles) of 2,2,4-trimethyl-1,3-pentane diol and 0.54 grams (0.1 wt. %) of potassium hydroxide. The reactor was sparged with nitrogen and evacuated three times. After heating the contents to 100° C. under vacuum, the reactor was pressured to 10 psia with nitrogen, and heated to 150° C.

Ethylene oxide (264 grams, 6.0 moles) was added over one hour at 150°–160° C. and 50–60 psi. After an additional one hour reaction time, the contents were cooled to 100° C. and a vacuum was pulled to remove any residual ethylene oxide. The product was a clear liquid which had a hydroxyl value of 428 determined by acetylation on a hotplate and titration using KOH (Reference: ASTM Test E222, Method B).

EXAMPLE 2

The following are examples of fabric softener formulations prepared in accordance with the present invention.

| FORMULATION A | |
|---|---|
| Component | % by Weight |
| Disofttallowdimethyl ammonium chloride 75 wt. % in isopropanol ("Adogen 470", Witco Corp.) | 50.0 |
| Diol alkoxylate formed by alkoxylating 2,2,4-trimethyl-1,3-pentane diol with one mole of ethylene oxide | 12.5 |
| Deionized water | 37.5 |
| Total | 100.0 |

Procedure: The diol alkoxylate was blended with the quaternary ammonium compound, and then water was added, with light stirring until the mixture was homogeneous. All ingredients were added and combined at 20° C. The resulting product was a high solid content, clear, homogeneous liquid formulation.

| FORMULATION B | |
|---|---|
| Component | % by Weight |
| Dihardtallowdimethyl ammonium chloride, 75% solution in isopropanol ("Adogen 442", Witco Corp.) | 3.4 |
| 2,2,4-trimethyl-1,3-pentanediol | 1.1 |
| Deionized water | 95.5 |
| Total | 100.0 |

The quaternary ammonium compound was blended with the $C_8$ diol and this blend was added to the water at 90° F. with light agitation until the materials were completely dispersed. The resulting product was a cloudy, emulsion-type yet almost clear, liquid composition with a viscous appearance. This example demonstrates yet a further advantage of the present invention, namely that employing the diol alkoxylates as described herein permits the preparation of a cationic composition having a given viscosity with the use of a smaller amount of cationic component than would be necessary to achieve that given viscosity level using the same cationic component without using the diol.

The viscosity of Formulation B was about 175 cps, whereas the viscosity of the "Adogen 442" alone, at the same level of quaternary in water, is about 15 cps.

| FORMULATION C | |
|---|---|
| Component | % by Weight |
| Dimethylbis(softtallowamidoethyl)-2-hydroxyethylammoniummethylsulfate ("Varisoft 222 LM-90", Witco Corp.) | 80.0 |
| Diol alkoxylate produced by ethoxylating 2,2,4-trimethyl-1,3 | 20.0 |

-continued

FORMULATION C

| Component | % by Weight |
|---|---|
| propane diol with 2-moles of ethylene oxide | |

This product is a non-aqueous concentrate which is readily dispersible in water at a temperature down to 45° F. Such dispersion produces readily a homogeneous, liquid cationic composition which is uniform in appearance. This product can be diluted, or used as is, in industrial and institutional applications as well as in household applications as a fabric softener or textile finishing agent.

FORMULATION D

| Component | % by Weight |
|---|---|
| Methyl-1-oleylamidoethyl-2-oleylimidazoliniummethylsulfate ("Varisoft 3690", Witco Corp.) 90% in isopropanol | 75.0 |
| Diol alkoxylate produced by ethoxylating 2,2,4-trimethyl-1,3-propanediol with 2 moles of ethylene oxide | 25.0 |

The indicated components were blended together at room temperature, which readily produced a cationic formulation, useful as a fabric softener, paper debonder or textile finishing agent, having a relatively high concentration of active ingredient and which exhibited a homogeneous, uniform appearance. This product could easily give a very clear final formation, and can be diluted easily to below 10% solids for a clear, thick, low solids softener, or can be used with 3–6 % additional isopropanol or ethanol as solvent to form a 40–50 % clear, ultra concentrate for the household market.

Among the advantages of the present invention is the high degree of dispersibility in water, even cold or room temperature water, and the resultant ability to formulate from a more highly concentrated form to any target concentration level in water (even room temperature) regardless of temperature with only minimal agitation. Other advantages include odor and low cost effectiveness compared to conventional coupling agents. The lack of formation of a gel phase during dilution or dispersion of the material in water is believed to be due to the material forming very fine particles when added to cold water; this feature also improves fabric softener performance in the washing machine, and provides freedom from having to add salts for adjustment of viscosity. Salts such as $CaCl_2$ may be added to reduce viscosity in those formulations where lower solids "clear" formulations are being produced. Additional advantages include the clarity of the final composition and freedom from having to include excess volatile organic components in the product.

Cationic emulsions are normally unstable, especially when subjected to freezing and thawing, and have shelf lives of only 3–5 months. On the other hand, emulsions utilizing diol or diol alkoxylate of formula (1) exhibit much longer-term stabilities and better stability against freeze-thaw cycles. They also show good viscosity stability as well in dispersions up to about 10–15 wt. % in most cationic quaternary systems.

Additional Practical Exemplification

Laboratory work with compositions according to the present invention has demonstrated numerous specific advantageous aspects including, but not limited to, those set forth as follows.

The diols of formula (1), particularly TMPD, reduce the melting point of the quaternary component; this feature greatly assists dispersibility of the cationic agent in water. Thus, for any given water temperature, the quaternary component can be dispersed more readily and in a larger amount, if desired—when one or more components of formula (1) is present. The presence of the diol or diol alkoxylates also enables water to be added to the quaternaries and cationics, as well as the customary mode of adding the material to the water. This is unprecedented, as normally most quaternaries will gel if water is added to them as the quaternary solids content go to below 40%.

The diols and diol alkoxylates increase the viscosity of some formulations of quaternary compounds, easily by 10-fold or more. For a given content of quaternary compound(s), there is generally a range of the diol/diol alkoxylate component within which optimum high viscosity is exhibited; higher amounts of diol/diol alkoxylate with respect to the amount of quaternary present can reduce the viscosity compared to that obtained at lower diol and diol alkoxylate levels, and thereby form easily dispersed formulations.

Softening Performance

It has been determined that cationic formulations containing diol and/or diol alkoxylate of formula (1) provide fabric softening performance which is superior to that provided by comparable formulations without the diol/diol alkoxylate. Superior performance has been exhibited when the formulation used a $C_7$–$C_{12}$ diol. Typical results are in the following table:

| Comparison of Softening Performance with TMPD vs. Emulsions w/o TMPD (All tests used quaternary as 0.1 wt. % of fabric weight.) | | | |
|---|---|---|---|
| Softener | Wt. % of active in deionized water | Ratio (wt. %) of Quat.: TMPD | Softening Rank |
| | | | (5 = Best) |
| Di (hydrogenated tallow)-dimethyl ammonium chloride (as 75% formulation in isopropanol) (Adogen "442") | 3% | — | 3.1 |
| | 3% | 4:1 | 3.8 |
| | 3% | 3:2 | 4.1 |
| | | | (3 = Best) |
| Methyl-1-tallow amidoethyl-2-tallow-imidazolinium-methyl sulfate ("Varisoft 475-90") | 23.3% | — | 1.3 |
| | 26.8% | 3:2 | 1.7 |

In these experiments, all quaternary concentrations were held exactly equivalent; and the experiments were performed using identical testing conditions. Thus, any performance improvement is attributed to the presence of the TMPD.

These data confirm that the presence of the diol contributes additional fabric softening capability to the formulated product.

Clear Formulations

Formulations in accordance with this invention which exhibit acceptable clarity can be obtained with appropriate balance of the amounts of the softener and diol/diol alkoxylate components, the amounts of other components such as electrolytes, and the conditions (especially temperature) under which the formulations are prepared. In general, at lower softener contents, a higher ratio of TMPD or other diol and/or diol alkoxylate to the system needs to be observed. Additional examples of formulations according to this invention are:

NONFLAMMABLE IMIDAZOLINIUM QUATERNARY FORMULATION (useful as e.g. fabric softener, textile finishing, paper debonder)

A. Concentrate

80% Methyl-1-tallow amidoethyl-2-tallow imidazolinium methyl sulfate ("Varisoft 475")(as 90% conc. in isopropanol)
15% TMPD
5% $H_2O$ This product exhibits the following beneficial properties:
Dispersible in room temperature water
Non-flammable
Easy to handle
No need to heat or store the product at elevated temperatures
Stable dispersions at from 1–12% solids
Superior softening and antistatic properties vs. softener without the diol
Good rewettability
Thick viscosity at about 5–8% solids

| Typical Properties | |
|---|---|
| Appearance | light yellow liquid |
| Total Solids (%) | 72% |
| Density (gm/cc) | .92 |
| Flash Point (PMCC) °F. | >200° F. |
| B. Formulations for Use | | | |

| Wt. % of solids: | 3% | 5.5% | 8% |
|---|---|---|---|
| Approx. Viscosity (cps.) | 20 | 75 | 600 |
| % Quat: | 4.3% | 7.85% | 11.4% |
| % Tap Water | 95.7% | 92.15% | 88.6% |

Procedure for concentrate dilution:

Measure water required for dispersion into a suitable mixing vessel. Water temperature should be above 70° F. Add room temperature quaternary to the water with mild agitation. Continue agitation for 15 to 30 minutes until the softener is completely dispersed. Add dye, fragrance and preservative as required or needed. Solids of greater than 7% may need to be thinned using a $CaCl_2$ brine. Small amounts (less than 0.5% $CaCl_2$) should be used.

HIGH VISCOSITY/LOW-SOLIDS QUATERNARY FORMULATION

A. Concentrate 42.5% Methyl bis (tallow amidoethyl) 2-hydroxyethyl ammonium methyl sulfate ("Varisoft 222 LM-90") (as 90% conc. in isopropanol)

42.5% "Adogen 442" (as 75% conc. in isopropanol) 15% TMPD

This product exhibits the following beneficial properties:
Good softening and antistatic control
Easy to handle (fluid at 60°F.)
Dispersible at water temperature as low as 65° F.
High viscosity at less than 4% solids
Good formulation stability down to 1%
Can achieve elevated viscosity when Quat is dispersed at water temperatures below 75° F.

| Typical Properties | |
|---|---|
| Appearance | light yellow liquid |
| Pour Point (°F.) | 50° |
| Flash Point (PMCC) °F. | 86° |
| % IPA | 10° |
| Total solids (%) | 70% |
| Solids Formulation Range (%) | .5 to 8% |
| B. Typical End-Use Formulations | | | | |

| Solids Content | 2.5% Solids | | 4% Solids | |
|---|---|---|---|---|
| Dispersion Water Temp. (°F.) | >75° F. | <75° F. | >75° F. | <75° F. |
| Viscosity of Formulation, cps | 15 | 150 | 180 | 400 |
| Formulation: | | | | |
| % Product | 3.6% | | 5.7% | |
| % Water | 96.4% | | 94.3% | |

Procedure:

Measure water at desired temperature (to achieve desired viscosity) into a vessel equipped with a mixing agitator. Add room temperature quaternary (70°–80° F.) slowly to water under agitation. Mixing smoothly without whipping air into the dispersion reduces foam problems and having air contained in the thicker dispersion. Agitate until completely dispersed—usually 15–30 minutes depending on the type of agitation. Add dye, fragrances, preservatives as desired. If foam develops during mixing or bottling, add a few ounces of defoamer such as Antifoam B (Dow Corning).

"CLEAR" (ADJUSTABLE VISCOSITY) SOFTENER FORMULATION

A. Concentrate

80% Ditallow dimethyl ammonium chloride ("Adogen 470") (as 75% conc. in isopropanol)
20% TMPD This product exhibits the following beneficial properties:
Excellent softening with good antistatic control
Clear formulation
Variable solids content from 10 to 40% or greater
Easy to handle
Can be used as a "dilutable" to form a thick emulsion-type product when added to water down to 3–6% solids
Versatile viscosity from thin to thick using e.g. $CaCl_2$ as thinning agent
Can be used to form cold-water-dispersible formulations of 4–6% solids (viscosity of 70–200cps)
Great dispersibility in cold water

| Typical Properties | |
|---|---|
| Appearance | Clear yellow fluid liquid |
| Total solids (%) | 58% |
| Density (gm/cc) | 0.87 |
| Flash point (PMMC) | 70° F. |

| Typical Properties | |
|---|---|
| Min. Handling Temp. (°F.) | 40 |
| Cloud Point (°F.) | 45 |

B. Typical End-Use Formulations

| | 18–20% | 24–26% solids | 30–35% solids |
|---|---|---|---|
| Concentrate | 33% | 42% | 52% |
| CaCl₂ | .05–.15% | .2–.4% | .02–.125% |
| Water | Balance to 100% | | |
| Dye, Preservative and Fragrance | As desired or recommended by suppliers | | |

Procedure:

Charge water into a suitable mixing vessel. Add proper level of CaCl₂ to obtain stable, clear final softener formulation. Add all required Quat to water and begin to agitate. Upon mild agitation a "clear" fluid (or viscous if desired) softener formulation will form. Initially during blending, periods of hazy or even opaque dispersion may exist prior to "clearing." Too much CaCl₂ should be avoided as it will lead to splitting out of the softener. Too little CaCl₂ will result in high viscosity or even a gel. If too much CaCl₂ is added, water can be added diluting the formulation and switching the formulation back to a clear formulation.

HAIR CARE CONDITIONER (9 wt. % solids)

| | Ingredient | Amount (wt. %) |
|---|---|---|
| I: | Deionized water | 90.0 |
| | Quaternium 10 (polymeric quaternary ammonium salt of hydroxyethyl cellulose reacted with trimethyl ammonium-substituted Hydroxyethylcellulose | 0.5 |
| | Hydroxyethylcellulose | 0.5 |
| | Glycerine | 1.6 |
| II: | "Adogen 442" (as 75% conc. in isopropanol) | 3.5 |
| | TMPD × 1-mole ethoxylate | 1.4 |
| | Oleth-2 (oleyl alcohol × 2-mole ethoxylate) | 1.5 |
| | Hydrogenated coconut oil | 1.0 |
| III. | Preservative | q.s. |

Mixing instructions: Mix I, until uniform, then heat to 70° C. Mix II. to uniformity and heat to 70° C. Add II. to I. with agitation. Add III. Cool, with mixing, to 30° C.

| Ingredient | Amount (wt. %) |
|---|---|
| PAPER DEBONDERS | |
| | A |
| Di(hard tallow) dimethyl ammonium methyl sulfate | 50 |
| TMPD | 20 |
| TMPD × 2-mole ethoxylate | 20 |

| Ingredient | Amount (wt. %) |
|---|---|
| Water | 5 (melts at 75–80° F.; dispersible in 85° F. water) |
| | B |
| Methyl-1-oleyl amidoethyl-2-oleyl imidazolinium methylsulfate | 80 |
| TMPD | 10 |
| TMPD × 1-mole ethoxylate | 10 |
| NON-FLAMMABLE TEXTILE FINISHING FORMULATION | |
| Methyl bis (tallowamidoethyl)-2-hydroxyethyl ammonium methylsulfate (as 85% conc. in hexylene glycol) | 81 |
| TMPD | 14 |
| Water | 5 |
| Approximate pour point = 55° F. | |
| Approximate minimum water disposal temperature = 50° F. | |

What is claimed is:

1. A homogeneous liquid cationic composition comprising:

(a) one or more compounds of the formula (1)

$$HO(X-O)_x-R-(O-Y)_y-OH \qquad (1)$$

wherein each X is ethylene, straight or branched propylene, or straight or branched butylene;
   x is 0;
   each Y is ethylene, straight or branched propylene, or straight or branched butylene;
   y is 0; and
   R is saturated, straight, branched or cyclic alkylene containing 4 to 12 carbon atoms, provided that if x and y are both zero then R contains 7 to 12 carbon atoms; and (b) one or more cationic agents; and (c) water; wherein said component (b) comprises at least 25% wt. % of said composition.

2. A composition in accordance with claim 1 containing at least one compound according to formula (1) wherein x and y are both zero and R is branched noncyclic alkylene containing 7 to 8 carbon atoms.

3. A composition in accordance with claim 1 containing one or both of 2, 2, 4-trimethyl-1, 3-pentane diol and 2-ethylhexane-1, 3-diol.

4. A composition in accordance with claim 1 containing 2, 2, 4-trimethyl-1, 3-pentane diol.

5. A composition in accordance with claim 1 wherein said one or more cationic agents includes di(hydrogenated tallow) dimethyl ammonium chloride.

6. A composition in accordance with claim 1 wherein said one or more cationic agents includes methyl bis (tallowamidoethyl-)-2-hydroxyethyl ammonium methylsulfate.

7. A composition in accordance with claim 1 wherein said one or more cationic agents includes methyl-1-tallowamidoethyl-2-tallow-imidazolinium methylsulfate.

8. A composition in accordance with claim 1 wherein said one or more cationic agents includes one or more compounds selected from the group consisting of compounds of any of the formulas

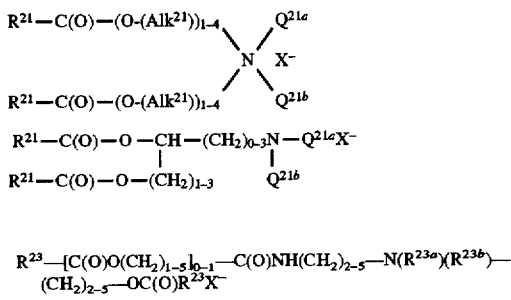

$$R^{23}-[C(O)O(CH_2)_{1-5}]_{0-1}-C(O)NH(CH_2)_{2-5}-N(R^{23a})(R^{23b})-(CH_2)_{2-5}-OC(O)R^{23}X^-$$

wherein each $R^{21}$ is independently a saturated or unsaturated alkyl or alkylene radical containing 12 to 22 carbon atoms;

$Q^{21a}$ and $Q^{21b}$ are alkyl containing 1 to 4 carbon atoms or benzyl, $—CH_2CH_2OH$, or $—CH_2CH(OH)CH_3$, or $Q^{21a}$ can be $R^{21}—C(O)—(O—(Alk^{21}))_{1-4}—$;

each $Alk^{21}$ is independently $C_2H_4$, $C_3H_6$ or $C_4H_8$;

$R^2$ is alkyl containing 1 to 4 carbon atoms or benzyl, $—CH_2CH_2OH$ or $—CH_2CH(OH)CH_3$;

each $R^{23}$ is independently straight or branched alkyl or alkenyl containing 8 to 22 carbon atoms;

$R^{23a}$ is straight or branched alkyl or hydroxyalkyl containing 1 to 3 carbon atoms, benzyl, or $—C_2H_4OC(O)R_4$ wherein $R^4$ is straight or branched alkyl or alkenyl containing 8 to 22 carbon atoms;

$R^{23b}$ is H, $—CH_3$, $—C_2H_5$ or benzyl; and $X^-$ is an anion.

9. A composition according to claim 1 wherein said component (b) comprises two or more cationic agents.

10. A composition according to claim 1 wherein said component (b) comprises at least 30 wt. % of said composition.

11. A composition according to claim 1 wherein said component (b) comprises at least 40 wt. % of said composition.

12. A composition according to claim 1 wherein said component (b) comprises at least 50 wt. % of said composition.

* * * * *

UNITED STATES PATENT AND TRADEMARK OFFICE
CERTIFICATE OF CORRECTION

PATENT NO. : 5,674,832
DATED : October 7, 1997
INVENTOR(S) : Robert O. Keys

It is certified that error appears in the above-identified patent and that said Letters Patent is hereby corrected as shown below:

Column 6, line 63: "A $\beta$" should read --A $\ominus$ --

Column 11, line 53: " X $^{31}$ " should read -- X $^{-}$ --

Column 19, line 42: after "substituted" insert -- epoxide) --

Column 19, line 60: insert the following:

-- Ingredient     Amount (wt.%) --

Signed and Sealed this

Nineteenth Day of January, 1999

Attest:

Attesting Officer

*Acting Commissioner of Patents and Trademarks*